US007773721B2

(12) United States Patent
Wu et al.

(10) Patent No.: US 7,773,721 B2
(45) Date of Patent: Aug. 10, 2010

(54) MULTI-SEGMENT CONE-BEAM RECONSTRUCTION SYSTEM AND METHOD FOR TOMOSYNTHESIS IMAGING

(75) Inventors: Tao Wu, Winchester, MA (US); Richard Moore, Concord, MA (US); Daniel Kopans, Waban, MA (US)

(73) Assignee: The General Hospital Corporation, Boston, MA (US)

( * ) Notice: Subject to any disclaimer, the term of this patent is extended or adjusted under 35 U.S.C. 154(b) by 712 days.

(21) Appl. No.: 10/578,295

(22) PCT Filed: Nov. 29, 2004

(86) PCT No.: PCT/US2004/039913

§ 371 (c)(1),
(2), (4) Date: Mar. 27, 2007

(87) PCT Pub. No.: WO2005/055803

PCT Pub. Date: Jun. 23, 2005

(65) Prior Publication Data

US 2007/0263765 A1      Nov. 15, 2007

Related U.S. Application Data

(60) Provisional application No. 60/526,719, filed on Dec. 3, 2003.

(51) Int. Cl.
*A61B 6/03* (2006.01)
(52) U.S. Cl. ..................................................... 378/21
(58) Field of Classification Search ............... 378/21–27
See application file for complete search history.

(56) References Cited

U.S. PATENT DOCUMENTS

| 5,872,828 | A | 2/1999 | Niklason et al. | |
| 6,529,575 | B1* | 3/2003 | Hsieh | 378/4 |
| 6,574,297 | B2 | 6/2003 | Tam | |
| 6,707,878 | B2 | 3/2004 | Claus et al. | |
| 2004/0225212 | A1 | 11/2004 | Okerlund et al. | |
| 2004/0264636 | A1* | 12/2004 | Claus et al. | 378/26 |
| 2005/0078862 | A1* | 4/2005 | Guillemaud et al. | 382/132 |

(Continued)

FOREIGN PATENT DOCUMENTS

WO    WO 2005/055803    6/2005

OTHER PUBLICATIONS

Villafana, AAPM Tutorial: Generators, X-ray Tubes, and Exposure Geometry in Mammography, 1990, Radiographics, vol. 10, pp. 539-554.*

(Continued)

*Primary Examiner*—Edward J Glick
*Assistant Examiner*—John M Corbett
(74) *Attorney, Agent, or Firm*—Quarles & Brady, LLP

(57) ABSTRACT

A tomosynthesis method for creating a three-dimensional reconstruction of a target element volume acquires radiation absorbance images of the target element volume through a limited plurality of positions. The target element volume is divided into a plurality of volume segments and a reconstruction algorithm is applied to each segment to generate a three-dimensional reconstruction of each volume segment. The three-dimensional reconstruction of each volume segment is then merged to create a three-dimensional reconstruction of the target volume. A tomosynthesis system and a computer program product for carrying out tomosynthesis are also provided.

21 Claims, 8 Drawing Sheets

U.S. PATENT DOCUMENTS

2005/0105679 A1    5/2005    Wu et al.

OTHER PUBLICATIONS

Bleut et al., An Adaptive Fan Volume Sampling Scheme for 3D Algebraic Reconstruction in Linear Tomosynthesis, Oct. 2002, Proceedings of the IEEE Nuclear Science Symposium and Medical Imaging Conference, vol. 49, Issue 5, Part 1, pp. 2366-2372.*

Smith et al., Fan-Beam Reconstruction from a Straight Line of Source Points, 1993, IEEE Transactions on Medical Imaging, vol. 21, No. 1, pp. 10-18.*

Magnusson Seger et al., Scanning of logs with linear cone-beam tomography, Available online May 23, 2003, Computers and Electronics in Agriculture, vol. 41, pp. 45-62.*

International Search Report, from related application PCT/US04/39913, mailed Aug. 9, 2005.

Lange, K. et al., "Globally Convergent Algorithm for maximum a Posteriori Transmission Tomography," IEEE Transactions on Image Processing 4:1430-1438 (1995).

Niklason, L.T. et al., " Digital Tomosynthesis in Breast Imaging," Radiology 205:399-406 (1997).

Written Opinion of the International Searching Authority, from related application PCT/US04/39913, mailed Aug. 9, 2005.

Wu, T. et al., "Tomographic Mammography Using a Limited Number of Low-Dose Cone-Beam Projection Images," Medical Physics 30(3):365-380 (2003).

* cited by examiner

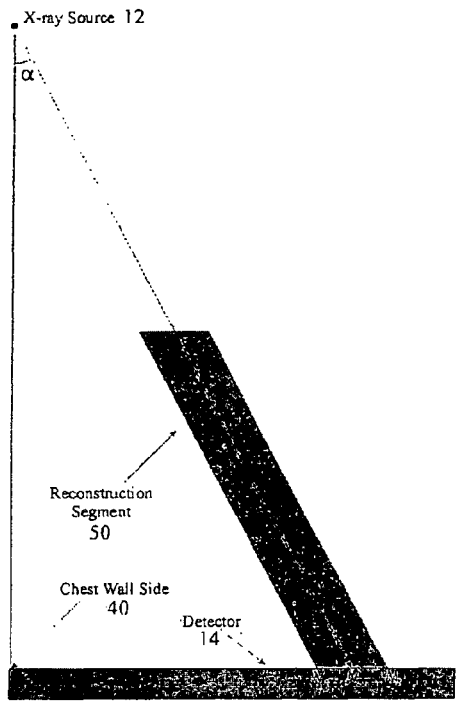

Legend for Figure 5

$N_1$: index of the first detector row in segment $N$
$N_2$: index of the last detector row in segment $N$
$N_c$: index of the center row in segment $N$
$N_1 = 25 \cdot N$
$N_2 = 25 \cdot N + 49$
$N_c = 25 \cdot N + 25$ The slope of the volume is represented by $\alpha$, the angle made by the detector plane and the line connecting the center of segment $N$ and the X-ray source at 0°:

$Tan(\alpha) = (Nc \cdot \Delta)/SD$
$\Delta$: detector pixel size
SD: source-to-detector distance

*Figure 5*

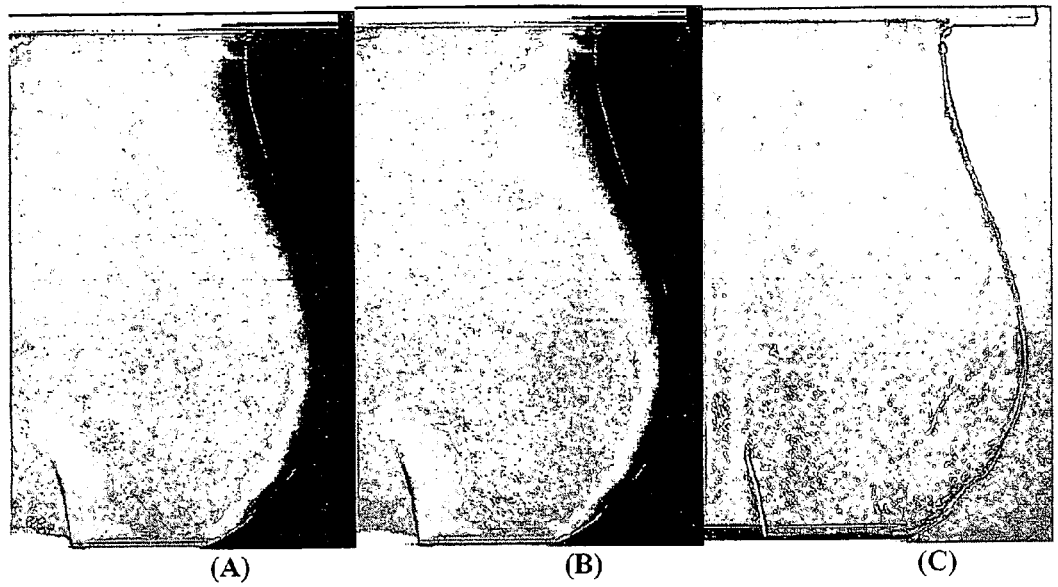
Figures 8A-C
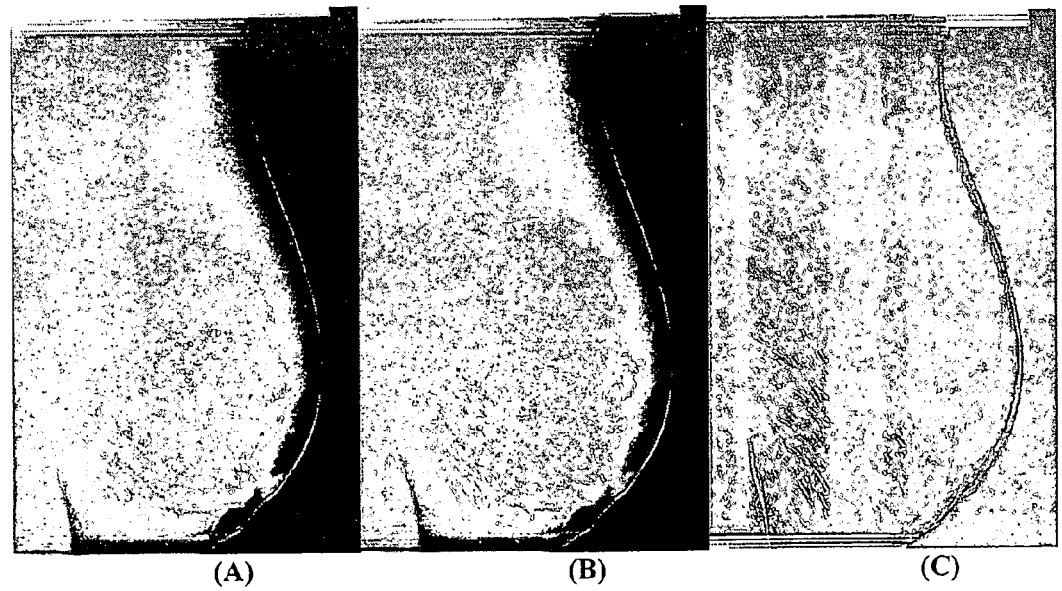
Figures 9A-C

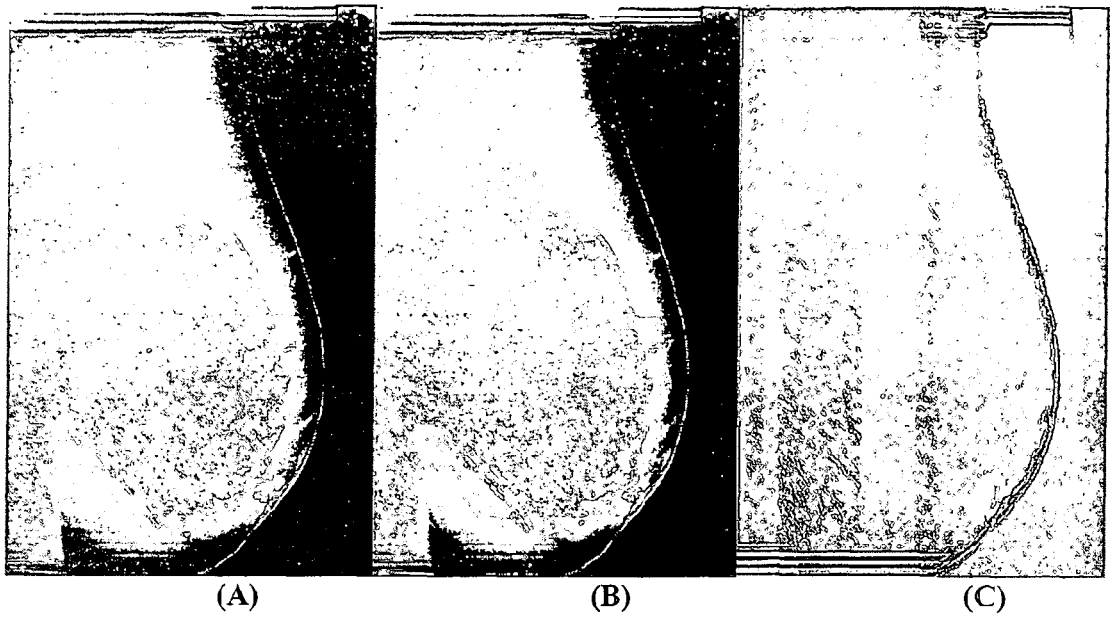
*Figures 10A-C*
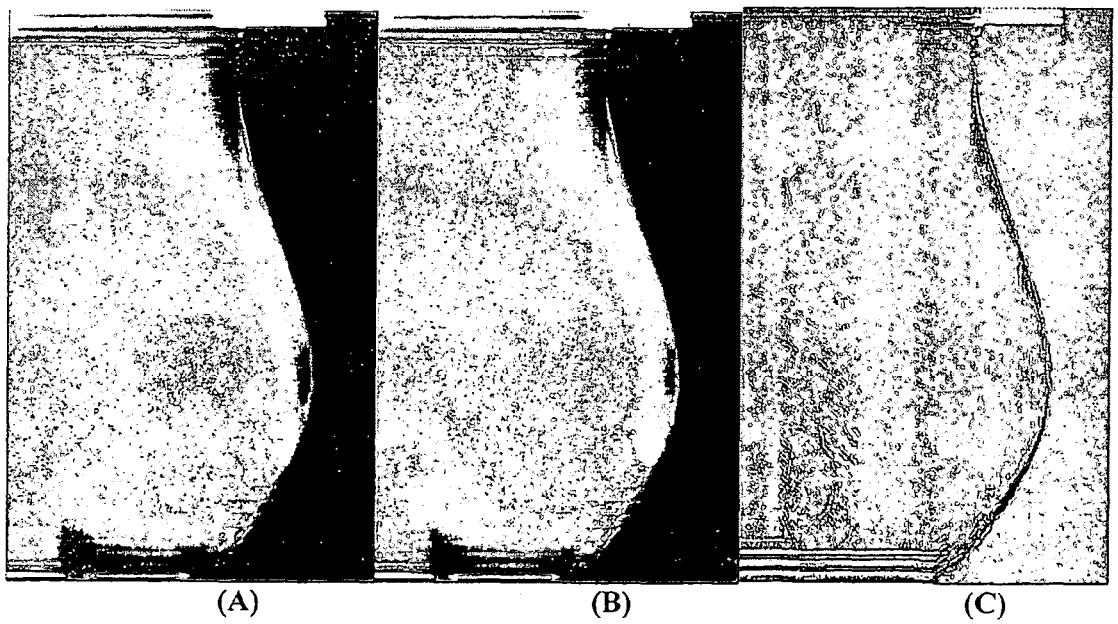
*Figures 11A-C*

MULTI-SEGMENT CONE-BEAM RECONSTRUCTION SYSTEM AND METHOD FOR TOMOSYNTHESIS IMAGING

RELATED APPLICATIONS

This application claims priority to U.S. Provisional Application No. 60/526,719, entitled Multi-Segment Cone-Beam Reconstruction Algorithm for Tomosynthesis Imaging and filed on Dec. 3, 2003, which application is incorporated herein by reference.

FIELD OF THE INVENTION

The present invention relates to a system and method for imaging a target element using tomosynthesis. More specifically, the invention relates to a system, method and computer program product for creating a three-dimensional image of target elements from a plurality of radiation absorbance projection images taken from different angles.

BACKGROUND OF THE INVENTION

Imaging of a patient's tissue has become a common screening and/or diagnostic tool in modern medicine. One example of such imaging is mammography, or the imaging of a patient's breast tissue. Breast cancer remains the most common cancer among women today, however, at this time there is no certain way to prevent breast cancer and the best strategy for dealing with breast cancer is early detection of the cancer so that it may be treated prior to metastatic spread. Accordingly, it is important for patients to have access to imaging techniques and systems that will detect very small cancers as early in their development as possible.

A three-dimensional imaging approach called "tomosynthesis" has been developed (see U.S. Pat. No. 5,872,828, which is incorporated herein by reference for its teachings relating to tomosynthesis systems and methods) which shows great promise for early detection of cancer. Tomosynthesis allows the reconstruction of a true volumetric distribution of absorption coefficients on the basis of the information contained in a series of projections acquired from a series of viewpoints about the target object. The viewpoint need not be regularly spaced, numerous, or arranged in any regular geometry. The tomosynthesis technique has been demonstrated to provide useful spatial differentiation of overlapping and nearby tissues at very high resolution comparable to projection 2D imaging, with approximately comparable radiation dose.

The problem of 3D reconstruction from tomosynthesis projections is difficult one. One promising technique for 3D reconstruction from tomosynthesis projections is provided in U.S. Provisional Patent Application Ser. No. 60/446,784, which is incorporated herein by reference. This technique applies a cone-beam geometry in an iterative forward-projection and back-projection method based on maximum-likelihood estimation of volumetric distribution of attenuation coefficients, using an estimation-maximization algorithm. However, the amount of computing power required to perform the 3D reconstruction will, for typical inexpensive computer systems, result in significant delays before the 3D reconstruction is available.

SUMMARY OF THE INVENTION

The present invention improves upon systems and methods known in the art by providing tomosynthesis apparatus and techniques for three-dimensional imaging of target elements that overcome the problems of conventional three-dimensional imaging systems and enable the use of tomosynthesis to efficiently provide accurate three-dimensional imaging of a target element in a shorter time than has previously been possible. The invention can increase the speed of the overall volume reconstruction by applying a segmentation of the target volume, while providing a quality of reconstruction that is substantially the same as for reconstructions that do not employ the segmentation algorithm of the invention. In preferred embodiments, the invention directs the reconstruction of volume segments to a multiplicity of CPUs within a multi-CPU computer cluster so that the volume segments can be reconstructed simultaneously in a parallel architecture. In further preferred embodiments, the volume segments are selected to be optimally overlapping in order to provide mutual boundary coverage of what would otherwise be under-determined edge volume segments.

In one aspect, the invention provides a tomosynthesis method for creating a three-dimensional reconstruction of a target element volume through the acquisition of radiation absorbance projection images of the target element volume through a limited plurality of viewpoints. The target element volume is divided into a plurality of volume segments and a reconstruction algorithm is applied to each segment to generate a three-dimensional reconstruction of each volume segment. The three-dimensional reconstruction of each volume segment is then merged to create a full three-dimensional reconstruction of the target volume.

In a further aspect of the invention, a system for three-dimensional tomosynthesis imaging of a target element is provided having an image acquisition element and a processor. The image acquisition element obtains a plurality of images of the target element from a plurality of viewpoints. The image acquisition element includes a radiation source positionable at a plurality of viewpoints with respect to the target element and a radiation detector. The radiation detector is positioned so as to detect radiation emitted by the radiation source passing through the target element and determine a plurality of attenuation values for radiation passing through the target element to establish a radiation absorbance projection image of the target element for a particular radiation source position. The processor is configured to apply a reconstruction algorithm to the radiation absorbance projection images of the target element obtained from a plurality of radiation source positions to generate a three-dimensional reconstruction of the target element. The processor is further configured to divide the target volume into a plurality of image reconstruction volume segments for separate image reconstruction of the volume segments and to merge the reconstructed volume segments into a three-dimensional reconstruction of the target element.

In a still further aspect, the invention provides a computer program for three-dimensional tomosynthesis imaging of a target element volume from a plurality of radiation absorbance projection images obtained at different angles from an image acquisition element having a radiation source positionable at a plurality of viewpoints with respect to the target element and a radiation detector positioned so as to detect radiation emitted by the radiation source passing through the target element volume and determine a plurality of attenuation value for radiation passing through the target element to establish a radiation absorbance projection image of the target element volume for a particular radiation source position. The computer program code is embodied in a computer readable medium and includes computer program code for dividing the target element volume into a plurality of volume segments, applying a reconstruction algorithm to each segment to generate a three-dimensional reconstruction of each volume segment, and merging the three-dimensional reconstruction of each volume segment to create a three-dimensional reconstruction of the target volume.

BRIEF DESCRIPTION OF THE DRAWINGS

The invention will be more fully understood from the following detailed description taken in conjunction with the accompanying drawings, in which:

FIG. 5 illustrates diagrammatically a reconstruction segmentation that may be implemented in a method and system of the invention;

FIGS. 8A, 8B and 8C illustrate a reconstructed volume image slice at Z=10 mm for a convention reconstruction, a segmented reconstruction of the invention, and a difference between the two, respectively;

FIGS. 9A, 9B and 9C illustrate a reconstructed volume image slice at Z=30 mm for a convention reconstruction, a segmented reconstruction of the invention, and a difference between the two, respectively;

FIGS. 10A, 10B and 10C illustrate a reconstructed volume image slice at Z=50 mm for a convention reconstruction, a segmented reconstruction of the invention, and a difference between the two, respectively; and FIGS. 11A, 11B and 11C illustrate a reconstructed volume image slice at Z=70 mm for a convention reconstruction, a segmented reconstruction of the invention, and a difference between the two, respectively.

DETAILED DESCRIPTION

The systems and methods of the present invention improve upon systems and methods known in the art by providing tomosynthesis apparatus and techniques for three-dimensional imaging of target elements that overcome the problems of conventional three-dimensional imaging systems, including known tomosynthesis systems. The present invention enables the use of tomosynthesis to efficiently provide accurate three-dimensional imaging of a target element in a shorter time than has previously been possible. The invention includes an algorithm that is efficiently tuned by computationally appropriate segmentation of the target volume and directs the reconstruction of volume segments to a multiplicity of CPUs within a multi-CPU computer cluster so that the volume segments can be reconstructed in parallel. In a preferred embodiment, the volume segments are selected to be optimally overlapping in order to provide mutual boundary coverage of what would otherwise be under-determined edge volume segments. Thus it increases the speed of the overall volume reconstruction while providing a quality of reconstruction that is substantially the same as for reconstructions that do not employ the segmentation algorithm of the invention. The invention is applied below to one preferred embodiment in which the system is used for tomosynthesis mammography; however, the invention will be useful in a variety of three-dimensional imaging situations. For example, the invention can be applied to a variety of patient imaging problems such as heart imaging, or imaging of the soft tissues or bones of the hand. The imaging system of the invention can be used for diagnoses (as is described below for tomosynthesis mammography) or it may be used for other applications such as three-dimensional modeling for the purpose of fitting an implant (whether orthopedic, such as a hip or knee implant, an artificial heart, or other type of implant) or for use in surgical navigation systems.

1. INTRODUCTION TO AN EXEMPLARY TOMOSYNTHESIS MAMMOGRAPHY SYSTEM

Figure 1A:
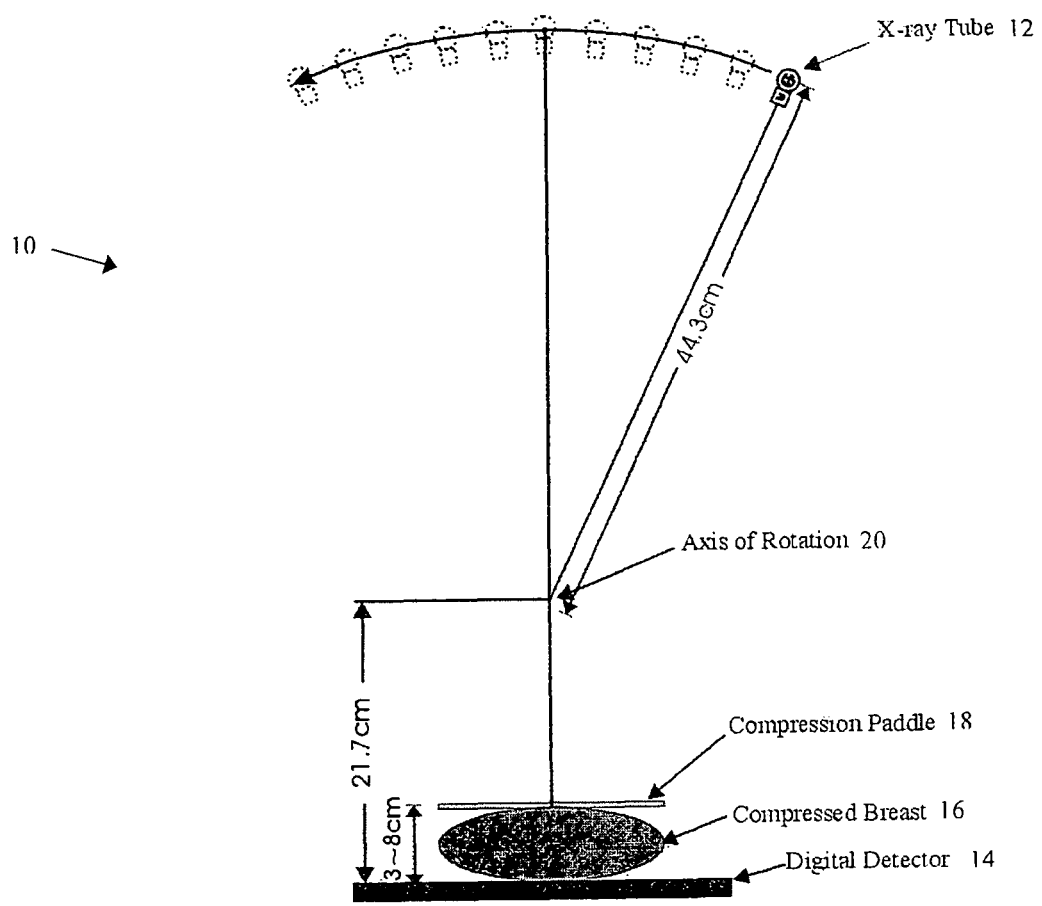
FIG. 1A provides a schematic of a tomosynthesis system according to one aspect of the invention.

Tomosynthesis mammography is a three-dimensional breast imaging technique. It involves acquiring projection images of a breast at a plurality of viewpoints, typically over an arc or linear path. Three-dimensional distribution of x-ray attenuation coefficient of the breast volume is reconstructed from these projections. An exemplary Tomosynthesis system 10 of the invention for breast imaging is illustrated in FIG. 1A. Tomosynthesis system 10 includes an X-ray radiation source or tube 12 which is generally directed toward a detector, in this example, digital detector 14. The tissue to be imaged, in this example compressed breast tissue 16 compressed by compression paddle 18, is located between X-ray source 12 and digital detector 14 so that the attenuation of a signal from the X-ray source and passing through the tissue can be measured by the detector.

X-ray source 12 is rotatable about axis of rotation 20 in order to image compressed breast 16 from a plurality of angles. For this particular system 10, X-ray source 12 is located 44.3 cm from axis of rotation 20 while the axis of rotation is located 21.7 cm above digital detector 14. In this embodiment, eleven projections are acquired by moving X-ray source 12 over a 50° arc (−25° to +25°) above breast 16 in 5° angular steps. Breast 16 and detector 14 are stationary during the image acquisition. While in this embodiment the X-ray source 12 is rotatable within a plane to different angles, it should be understood that the source could be positioned so as to project images from a variety of viewpoints within the scope of the invention.

Certain characteristics of this exemplary embodiment of a tomosynthesis system useful with the invention are described below:

Spatial resolution and contrast resolution: Tomosynthesis system 10 can use an amorphous-Silicon-based flat panel detector 14 on which a CsI crystal phosphor is grown epitaxially read out as 2304×1800 pixels (100 μm pixel pitch) via a TFT array. This particular detector has a linear response over exposure levels up to 400 mR and 12 bits of working dynamic range. The reconstructed volume obtainable can be presented as a series of adjacent planes, with each plane having about the same resolution as the detector (100 um), but with a depth resolution on the order of a millimeter.

Dose: The target/filter combination is Rh/Rh and the accelerating potential is 25~33 kVp to image breasts with 3~8 cm range of thickness. The total x-ray dose for acquiring 11 projections is approximately 1.5 times of that used for one film-screen mammogram. Each projection is a low dose breast image (approximately 1/11 of the does per projection).

Patient motion: Patient motion is reduced by fast image acquisition. Using cone-beam x-ray geometry and an area detector, a projection of the whole breast can be recorded with one x-ray exposure at each angle. For each projection, the exposure time is 0.1~0.2 s and detector readout time is about 0.3 s. Rotation to the next angle is performed during the detector readout. The total image acquisition time for 11 projections is about 7 sec. Breast compression also helps to reduce patient motion.

Image acquisition geometry: The design of Tomosynthesis system 10 is based on the conventional mammography system. The MLO views have been used in most cases since it provides the most complete coverage of the whole breast.

Digital tomosynthesis mammography is particularly well suited for removing the tissue-overlap, and therefore reducing false-positive and false-negative diagnoses of breast cancer. The geometry of the tomosynthesis mammography system 10 is further illustrated in FIGS. 1B and 1C which illustrate two orthogonal views of the tomosynthesis system geometry with the FIG. 1B view being along the patient's chest wall (with the X-ray source 12 traveling into and out of the page) and the FIG. 1C view being in a direction toward the patient's chest wall. The system 10 acquires 11 projection images of the breast and then reconstructs an estimate of the volumetric distribution of attenuation coefficients likely to have resulted in the measured projections. Each projection image consists of 2304×1800 100 μM pixels. The thickness of compressed breasts ranges from <25 mm to >80 mm, typically within this range. The chest-to-nipple distance ranges from <50 mm to >160 mm, but typically lies within this range. The reconstructed volume distribution consists can be represented by slices spaced 1 mm apart with 100×100 μm in-plane voxels. Therefore, the size of reconstruction image is (30~80)×2304×(500~1600). Using a PC with a 2.4 GHz CPU, the reconstruction of a breast volume takes up to 5 hours. This is far to long for clinical use. One goal of this invention is to reduce the reconstruction time to a few minutes. This will not only permit clinical care, but will allow "real-time" needle placement to guide biopsies, etc.

2. VOLUME SEGMENTATION

Projection images can be divided into a series of stripe-like segments, parallel or curvilinear oriented along the chest wall, from the chest wall to the nipple. Each projection segment covers part of the whole breast volume. With appropriate segmentation, projection segments will continuously inform the whole breast volume. The complete or partial volume can be composed by careful assembly and blending results of segment reconstructions. Increasing the number of segments results in smaller segmented volume coverage and faster reconstruction.

Segmentation can be particularly useful in a parallel computing approach to image reconstruction. A parallel computing reconstruction can be developed and implemented on a computer cluster with, for example, 32-64 processors. In parallel computing reconstruction, the computation task is divided into independent smaller tasks, each of which reconstructs a part of the whole breast accomplished by one processor of the computer cluster. The volume image of the whole breast can be retrieved from the results of the small tasks. In the Tomosynthesis methods and systems of the invention, reconstruction of segments can be divided among a number of processors so that the segment reconstructions can be performed in a simultaneous, parallel fashion.

Figures 1B, 1C:
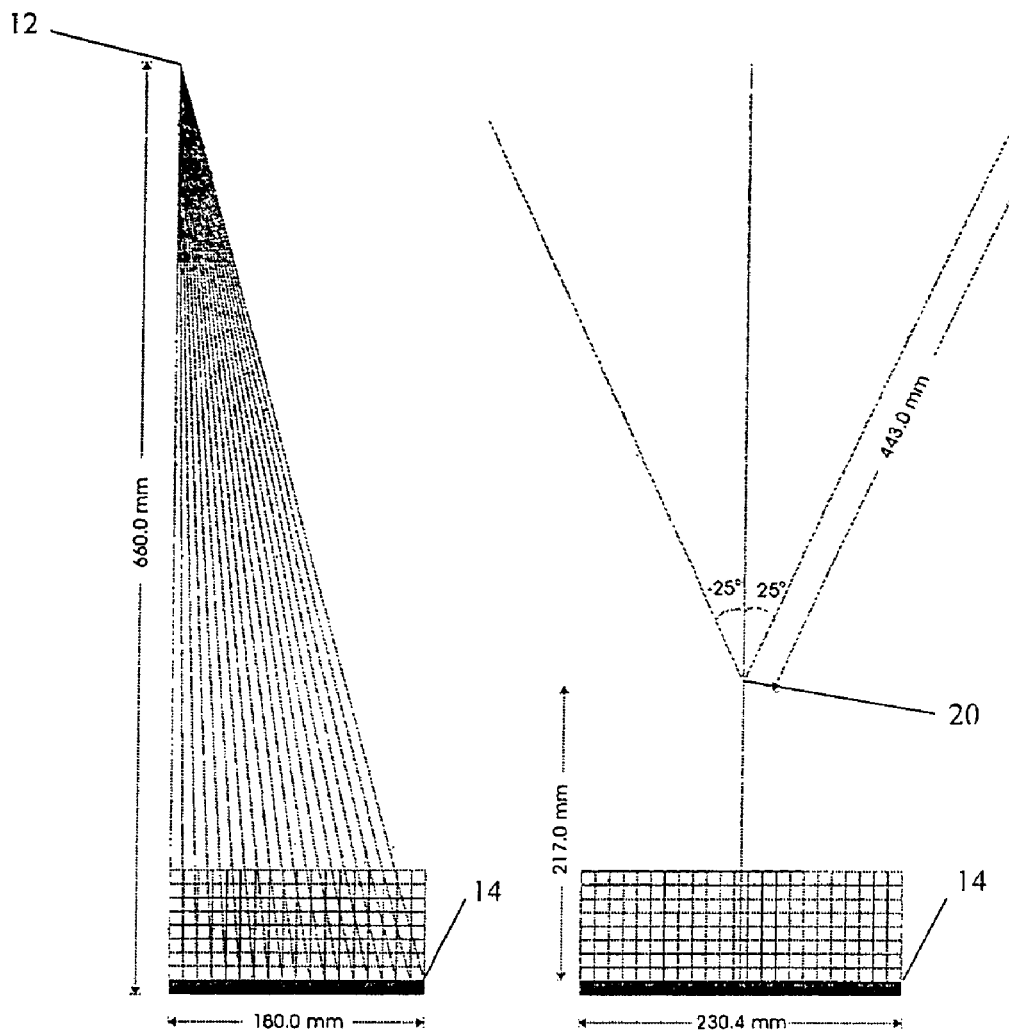
FIGS. 1B and 1C illustrate two orthogonal views of the geometry of the tomosynthesis system of FIG. 1A with the view of FIG. 1B being along a patient's chest wall (with the X-ray source traveling into and out of the page) and the view of FIG. 1C being in a direction toward the patient's chest wall.
Figure 2:
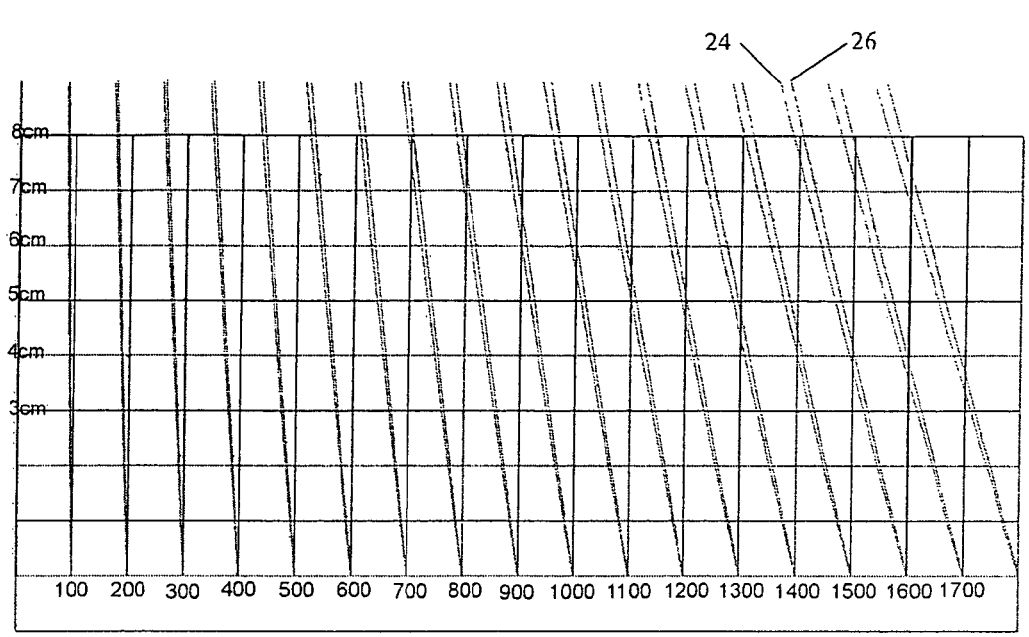
FIG. 2 illustrates segmented projections and volume coverage for the tomosynthesis system of FIG. 1A and from the perspective of FIG. 1B.

One method of segmentation, non-overlapping segmentation, can be illustrated by reference to FIG. 2, which provides a virtual view that is from the same perspective as the view of FIG. 1B. The vertical axis is the breast thickness dimension (Z axis, typically between about 3 and 8 cm in thickness as marked on the Figure). The horizontal axis is the chest-to-nipple direction (Y axis, typically about 1 to 17 cm, shown as columns 100-1700 for the illustrated detector). The motion of the X-ray tube is generally perpendicular to this Z-Y plane (the plane of the drawing sheet), with intersection between the Z-Y plane and the X-ray tube occurring at a tube rotation of 0° (Z=66 cm at 0° and Z=61 cm at ±25°). In this example, the projection image is divided into continuous, non-overlapping segments (the segments being represented by the columns graphically illustrated in FIG. 2) where each segment contains 100 columns. The volume coverage by each projection segment is shown by connecting the two edges of a segment (the bottom portion of each segment column illustrated in FIG. 2) to the X-ray source (the right-most line of each pair of lines connects to the source at 0° (one example marked as element 24 and the left-most line of each pair of lines connects to the source at 25° (one example marked as element 26)). There is a mismatch between the volume coverage at a source rotation of 0° and that of a source rotation of 25°. This mismatch is bigger for thicker breasts and for segments further away from the chest wall as shown in Table 1 below which shows the mismatch of volume coverage at source locations of 0° and 25°. In the worst case (8 cm thick breast, 16 cm from the chest wall), this mismatch is ~16 pixels. The mismatch of volume coverage indicates that, with this non-overlapping segmentation method, a small portion of the reconstructed volume (at the edge of the volume) will suffer from "missing projection data" within the segmented projection set.

TABLE 1

Mismatch of Volume Coverage by 0° and 25° Sources (with Pixel as Unit)

| Column | 3 cm | 4 cm | 5 cm | 6 cm | 7 cm | 8 cm |
|--------|------|------|------|------|------|------|
| 0 | 0 | 0 | 0 | 0 | 0 | 0 |
| 100 | 0 | 0 | 1 | 1 | 1 | 1 |
| 200 | 1 | 1 | 1 | 1 | 2 | 2 |
| 300 | 1 | 1 | 2 | 2 | 3 | 3 |
| 400 | 1 | 2 | 2 | 3 | 3 | 4 |
| 500 | 2 | 2 | 3 | 4 | 4 | 5 |
| 600 | 2 | 3 | 4 | 4 | 5 | 6 |
| 700 | 3 | 3 | 4 | 5 | 6 | 7 |
| 800 | 3 | 4 | 5 | 6 | 7 | 8 |
| 900 | 3 | 4 | 6 | 7 | 8 | 9 |
| 1000 | 4 | 5 | 6 | 7 | 9 | 10 |
| 1100 | 4 | 5 | 7 | 8 | 10 | 11 |
| 1200 | 4 | 6 | 7 | 9 | 10 | 12 |
| 1300 | 5 | 6 | 8 | 10 | 11 | 13 |
| 1400 | 5 | 7 | 9 | 10 | 12 | 14 |
| 1500 | 6 | 7 | 9 | 11 | 13 | 15 |
| 1600 | 6 | 8 | 10 | 12 | 14 | 16 |

Figure 3A:
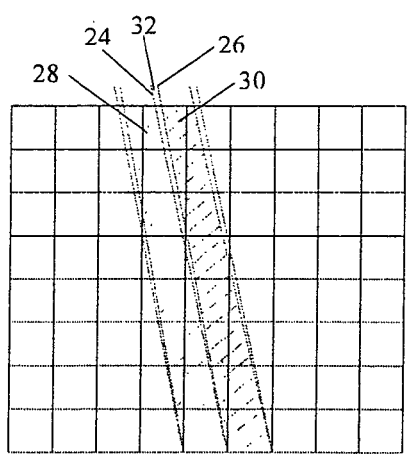
FIGS. 3A and 3B illustrate, respectively, non-overlapping and overlapping segmentation geometries that may be implemented in a method and system of the invention.
Figure 3B:
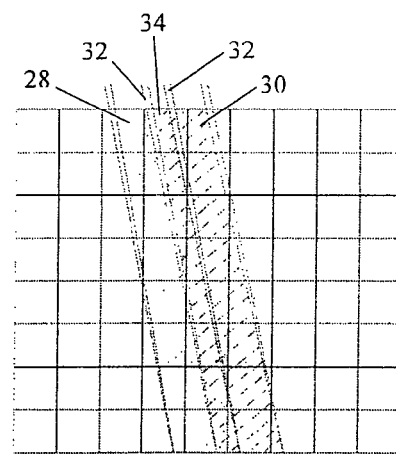

In the above example of non-overlapping segmentation, a small region of "bad volumes" occurs at the edge of the reconstructed volume. In FIG. 3A, the areas marked by cross-hatching 28, 30 represent "good volumes" and the gap 32 between them represents the "bad volume". Overlapping segmentation can be used to improve this situation. In this method—overlapping segmentation—a projection segment, illustrated in FIG. 3B, overlaps with its neighbor segments so that the volume coverage also overlaps. In FIG. 3B, projection areas 28, 30 marked by cross-hatching now overlap in overlap region 34. If the overlap of projection segments is big enough, "bad volumes" 32 will be located only in the overlapping regions 34. Therefore, a "bad volume" region 32 for one segment 28, 30 may overlap with a "good volume" region in a neighboring segment. Data describing the entire reconstructed volume can then be retrieved by using only "good volumes" and ignoring redundant "bad volumes."

3. PRELIMINARY RESULTS

50-Row Segments and 50% Overlapping

Figure 4:
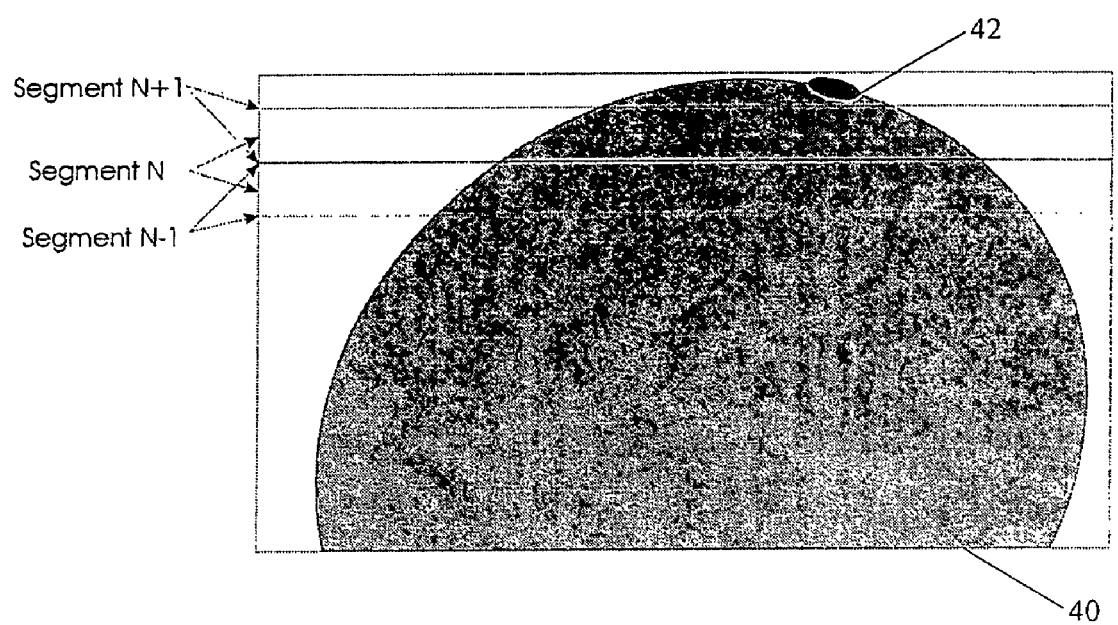
FIG. 4 illustrates diagrammatically a segmentation of a Tomosynthesis projection that may be implemented in a method and system of the invention.

Projection Segmentation:

An example of the system and method of the invention was implemented using segmented reconstruction with 50-row segments and a high 50% overlapping. Projections were divided into multiple segments (1 to N+1) as illustrated in FIG. 4 from the chest wall edge 40 to the nipple edge with the chest wall at the bottom of the Figure (the geometry of FIG. 4 is thus rotated 90 degrees counter-clockwise with respect to FIGS. 1B, 2, 3A and 3B). Each segment consists of 50 detector rows. The first 25 rows of segment N overlapped with the last 25 rows of segment N−1 and the last 25 rows of segment N overlapped with the first 25 rows of segment N+1. Accordingly, as shown in FIG. 5, $N_1$, the index of the first detector 14 row in a segment N, will equal 25*N; $N_2$, the index of the last detector 14 row in the segment N, will equal 25*N+49; and $N_c$, the index of the center detector 14 row in a segment N, will equal 25*N+25. The total number of segment was determined by the size of the breast from chest wall to nipple. If the projection consists of M rows, the number of segments will be 2×(M/50)−1. All the eleven projections were segmented in the same way.

The eleven projection segments with the same distance to the chest wall side were grouped into a set and used to reconstruct a volume segment. Reconstructed volume segments from all projection segments were then merged to form the whole breast volume. The reconstruction volume segment 50 from a projection segment had a "slanted rectangular" shape as shown in FIG. 5. The slope of the "slanted rectangular volume" was determined by the location of projection segments used to reconstruct this volume. The slope of the volume can be represented by angle α as shown in FIG. 5, where α is the angle made by the detector plane and the line connecting the center of segment N and X-ray source 14 located at a rotation of 0°.

A reconstructed volume segment had "bad voxels" close to its boundaries because the mismatch of volume coverage by between projection segments at different angles as shown in Table 1 above. However, the consecutive projection segments were overlapped by 50%, so the boundary of one segment was close to the center of a neighbor segment. The corresponding reconstructed volumes overlapped in a similar way and this 50% overlap was sufficient to place all "bad voxels" in overlapping regions. Therefore, a location taken by a "bad voxel" in one volume segment was overlapped by a "good voxel" in a neighbor volume segment so the whole breast volume can be retrieved with "good voxels".

Figure 6:
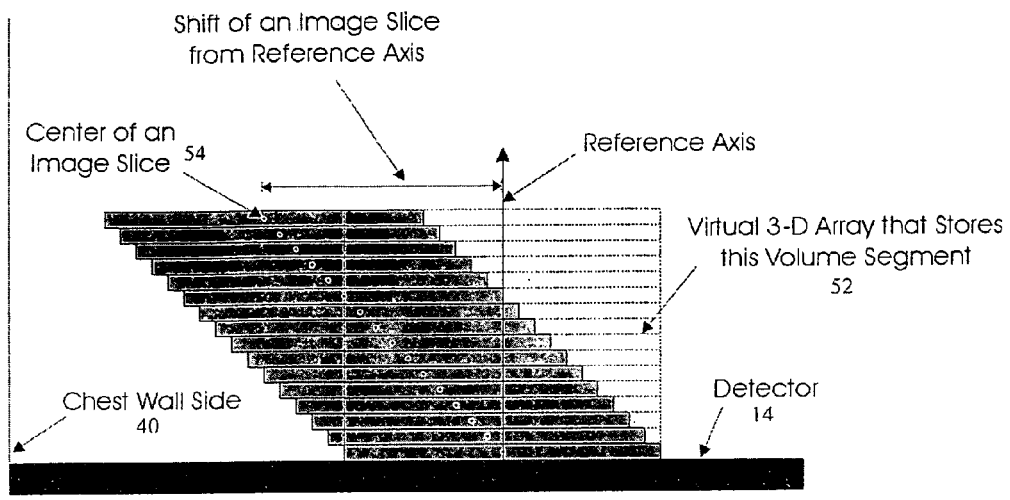
FIG. 6 illustrates diagrammatically a reconstruction of a volume segmentation that may be implemented in a method and system of the invention.

Reconstruction of Segmented Volume:

A segment of reconstruction volume was stored in a 3-D image array 52, as shown in FIG. 6, consisting of parallel image slices 54. Because the volume had a "slanted rectangular" shape (the line connecting the centers of image slices 54 points to the X-ray source), there was a shift between slice centers to form array 52. The implementation of the reconstruction algorithm was almost the same as that for the conventional reconstruction method, except that an extra operation (shift of slice center) was now taken in the calculation from volume index (i, j, k) to coordinate position (x, y, z) and vice versa. The value of the shift was determined by the slice position (the distance above the detector and the slope of the slanted volume) and the slope of the slanted volume varied for each volume segment (represented angle α in FIG. 5).

Figure 7:
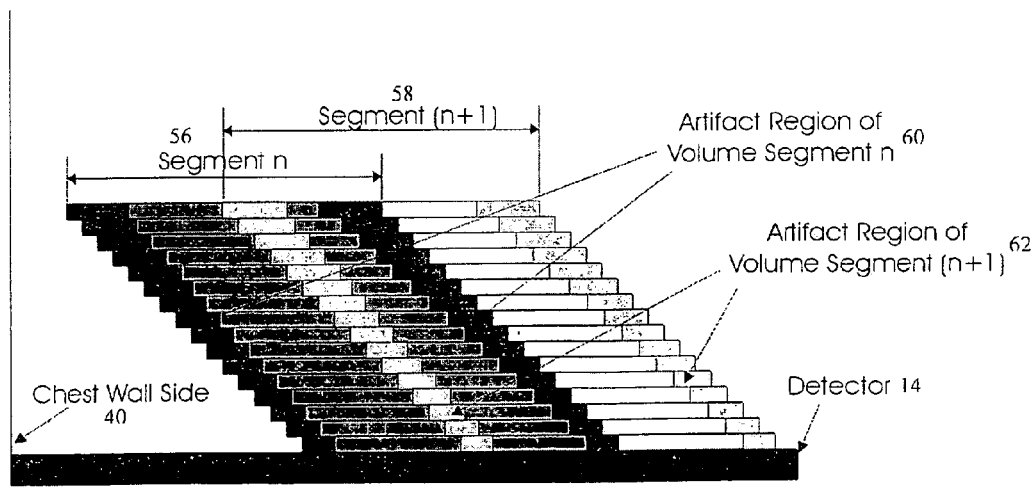
FIG. 7 illustrates diagrammatically a mergence of volume segmentations that may be implemented in a method and system of the invention.

Merging of Reconstructed Volume Segments:

When all the volume segments were reconstructed, they were merged to form the image of the whole breast volume. FIG. 7 shows the merging of two neighbor volume segments 56, 58. The two reconstructed segments had about 50% overlapping similar to the overlapping in projection segments. Bad voxels were in regions close to volume boundaries. However, the "bad voxel region" in one segment 60, 62 was covered by the "good voxel region" in a neighbor segment due to overlapping. The whole breast volume was then retrieved using only "good voxel regions".

4. PERFORMANCE OF THE INVENTION

A Tomosynthesis patient case was selected for performance test of a segmented reconstruction method of the invention. The thickness of the breast was 7 cm and the distance from the chest wall to nipple was ~14.5 cm. This was one of the larger target volumes from among those that had been imaged with the system of FIG. 1. Reconstructions were done with both a conventional (unsegmented) algorithm and the segmented algorithm for 9 iterations. The reconstruction volume was 2304×1450×70 (height, width and thickness) with a total size of ~450 MB. The workstation used for reconstruction had a Pentium III 866 MHz processor and 4 GB RAM.

For the conventional algorithm, it took ~53 min/iteration and a total of 8 hours for 9 iterations. For the segmented reconstruction algorithm, each projection was divided into 57 (2×[1450/50]−1) segments with a 50-row width. The first 25 rows of each segment were overlapped with the second 25 rows of the neighbor segment before it; and the second 25 rows of this segment was overlapped with the first 25 rows of the neighbor segment after it. The projection segments from different projections were grouped according to the distance from the chest wall. Therefore, 57 sets of projection segments were generated, each containing 11 projection segments with the same distance to the chest wall. Each set of the projection segments was used to reconstruct a volume segment. Each volume segment had 2304×50×70 voxels and took ~19 minutes for the total nine iterations (~2.1 min/iteration). Currently, the mergence of reconstruction segments takes ~5 minutes for this case. These reconstructions were done one by one using a single computer processor so the total reconstruction time is the summation of time used for all segments. When implementing the algorithm of the invention on a computer cluster, the total reconstruction time will be mainly determined by the time for the reconstruction of one segment.

Reconstructed volumes were compared. Four sets of reconstructed volumes were presented as slices (Z=10, 30, 50 and 70 mm) and are shown in FIGS. 8 through 11 illustrating these slices respectively. The images 8A, 9A, 10A and 11A are from the conventional reconstruction algorithm, the images 8B, 9B, 10B and 11B are from the segmented reconstruction algorithm and the images 8C, 9C, 10C and 11C are the difference between the conventional reconstruction and the segmented reconstruction. The value of most pixels of the difference images is less than 1% of the value of the corresponding reconstruction image pixel. The result demonstrates that images from the segmented reconstruction algorithm provide equivalent diagnostic information as those from the conventional reconstruction algorithm.

5. CONCLUSION

The segmented reconstruction method works successfully on a single processor system. In the test with a large-size target volume, the segmented reconstruction took 2.1 min/iteration for reconstruction with a 50-row projection segment and ~5 minutes to merge the reconstruction segments to form the whole target volume. The image quality of volumes formed from the segmented reconstruction method is equivalent to that from the conventional reconstruction method. If this method were implemented on a computer cluster with the same CPU (Pentium III, 866 MHz, 133 MHz bus speed, 133 MHz RAM speed) with a sufficient number of CPUs, the time for the whole reconstruction will be the same as the time for reconstructing one segment due to simultaneous, parallel processing. The total time for this case will be $$T=(2.1 \text{ min/iteration}) \times (\text{iterations}) + 5 \text{ min merging time} + \text{data transfer time}$$

The first two terms take ~25 minutes for this case on the current computer. Compared with 8 hours conventional reconstruction, segmented reconstruction reduces the time by a factor of 20 while providing diagnostic quality images. The typical breast size of a patient is about the half of this testing case.

Currently, computer clusters with 3 times faster processors (above 2.2 GHz, 266 MHz RAM, 533 MHz bus speed) are available. With such a system, the total time (reconstruction+merging+transferring) for a case is expected to be reduced to ~5 minutes for normal breast size and <10 minutes for very large size.

Advantages of the invention thus include fast computation speed for clinical applications with no loss of image quality. In addition, these performance increases can be provided with no increased cost at installations that already include multi-CPU computer clusters. Additionally, specialty FPGA arrays can be fabricated to implement multiple CPUs on a single PC add-in card. One or a series of these cards may employ the same strategy outlined above.

A person of ordinary skill in the art will appreciate further features and advantages of the invention based on the above-described embodiments. For example, specific features from the references incorporated by reference above may be incorporated into systems, methods or computer program products of the invention as well as features referred to in the claims below which may be implemented by means described herein and described in those documents. Accordingly, the invention is not to be limited by what has been particularly shown and described, except as indicated by the appended claims.

We claim:

1. A method for producing a three-dimensional tomosynthesis image of a target volume in a subject comprising:
    acquiring projection data from the target volume over a limited plurality of angles using a tomosynthesis imaging system;
    segmenting the acquired projection data into a plurality of partially overlapping volume segments such that neighboring volume segments each include projection data corresponding to the partially overlapping volume segments;
    applying a reconstruction algorithm to each volume segment to generate a plurality of reconstructed volume segments, each of the plurality of reconstructed volume segments including a central region and an underdetermined peripheral region; and
    merging the central regions of each reconstructed volume segment to produce the three-dimensional tomosynthesis image of the target volume.

2. The method of claim 1, wherein the three-dimensional image is formed from voxels corresponding to the central regions of the plurality of reconstructed volume segments.

3. The method of claim 2, wherein the three-dimensional image is not formed from voxels corresponding to the underdetermined peripheral region.

4. The method of claim 1, wherein the reconstruction algorithm includes a shift of slice center operation.

5. The method of claim 4, wherein a shift amount applied by the shift of slice center operation is determined by at least one of a distance of a portion of the target volume from a detector of the imaging system, a slope of slant of the portion of the target volume, and a slope of a slanted volume varied for each volume segment.

6. The method of claim 1, wherein the volume segments have a complex shape dependent upon an acquisition geometry and configured to allow reconstruction of a given volume segment independent of reconstruction of other volume segments.

7. The method of claim 6, wherein the volume segments have a slanted rectangular shape.

8. The method of claim 1, wherein the imaging system includes an x-ray source positionable at a plurality of angles relative to the subject.

9. The method of claim 1, wherein the plurality of partially overlapping volume segments overlap neighboring volume segments by a predetermined percentage.

10. The method of claim 9, wherein the predetermined percentage is less than 50 percent.

11. The method of claim 9, wherein the predetermined percentage is at least 50 percent.

12. A system for creating an image of a target element comprising:
    a tomosynthesis image acquisition element for obtaining a plurality of images of the target element from a plurality of angles having an x-ray source positional at a plurality of positions with respect to the target element and an x-ray detector positioned so as to detect x-ray emitted by the x-ray source passing through the target element and determine a plurality of attenuation values for x-ray passing through the target element;
    a processor system configured to receive an indication of the plurality of attenuation values as a plurality of imaging data sets and to:
        divide the plurality of imaging data sets into a plurality of partially overlapping volume segments;
        reconstruct each volume segment to generate a plurality of reconstructed volume segments, each of the plurality of reconstructed volume segments including a central region and an underdetermined peripheral region; and
        merge the central regions of each reconstructed volume segment to produce a tomosynthesis image of the target volume.

13. The system of claim 12, wherein the processor system comprises a plurality of processors configured to reconstruct each volume segment in parallel.

14. The method of claim 13, wherein the processor system comprises a number of processors that is at least equal to a number of image reconstruction volume segments divided.

15. The system of claim 12, wherein the image is not formed from voxels corresponding to the underdetermined peripheral region.

16. The system of claim 12, wherein the volume segments overlap by predetermined amount.

17. The system of claim 16, wherein the predetermined amount is less than 50 percent.

18. The system of claim 16, wherein the predetermined amount is at least 50 percent.

19. The system of claim 12, wherein the volume segments comprise have a complex shape dependent upon an acquisition geometry and configured to allow reconstruction of a given volume segment independent of reconstruction of other volume segments.

20. The system of claim 12, wherein reconstructing each volume segment includes performing a shift of slice center operation.

21. The system of claim 12, wherein a shift amount applied by the shift of slice center operation is determined by at least one of a distance of a portion of the target volume from a detector of the imaging system, a slope of slant of the portion of the target volume, and a slope of a slanted volume varied for each volume segment.

* * * * *